(12) United States Patent
Chin et al.

(10) Patent No.: US 10,602,920 B2
(45) Date of Patent: *Mar. 31, 2020

(54) MEDICAL DEVICE WITH OLED ILLUMINATION LIGHT SOURCE

(71) Applicant: Boston Scientific Scimed, Inc., Maple Grove, MN (US)

(72) Inventors: Yem Chin, Burlington, MA (US); Louis J. Barbato, Franklin, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 237 days.

This patent is subject to a terminal disclaimer.

(21) Appl. No.: 15/450,664

(22) Filed: Mar. 6, 2017

(65) Prior Publication Data
US 2017/0181610 A1     Jun. 29, 2017

Related U.S. Application Data

(60) Continuation of application No. 12/209,170, filed on Sep. 11, 2008, now Pat. No. 9,622,682, which is a
(Continued)

(51) Int. Cl.
*A61B 1/267*  (2006.01)
*A61B 1/06*  (2006.01)
(Continued)

(52) U.S. Cl.
CPC ........ *A61B 1/0684* (2013.01); *A61B 1/00096* (2013.01); *A61B 1/043* (2013.01);
(Continued)

(58) Field of Classification Search
CPC ............... A61B 1/0684; A61B 1/0686; G02B 2006/0096; G02B 6/04–08; F21V 2200/00–40
(Continued)

(56) References Cited

U.S. PATENT DOCUMENTS 4,769,292 A   9/1988  Tang et al.
5,315,129 A   5/1994  Forrest et al.
(Continued)

FOREIGN PATENT DOCUMENTS

DE    2152773 A1    4/1972
GB    2356464       5/2001
(Continued)

OTHER PUBLICATIONS

"Heat Transfer and Thermal Conductivity Are Not Linearly Related," Cool Polymers® Technical Bulletin, Insight on the use of thermally conductive plastics, vol. 1, No. 2, 2002, (4 pages).
(Continued)

*Primary Examiner* — Matthew J Kasztejna
(74) *Attorney, Agent, or Firm* — Bookoff McAndrews, PLLC

(57) ABSTRACT

A medical device such as a catheter or endoscope device includes an illumination light source having one or more organic light-emitting diodes (OLEDs). The OLEDs are energized to produce illumination light that is received by an image sensor or camera to produce images of tissue within a patient's body. A heat conductive polymer conducts heat away from the illumination light source.

18 Claims, 3 Drawing Sheets

Related U.S. Application Data division of application No. 10/737,980, filed on Dec. 17, 2003, now abandoned.

(51) Int. Cl.
*A61B 1/00* (2006.01)
*A61B 1/12* (2006.01)
*A61B 5/06* (2006.01)
*A61B 1/04* (2006.01)
*A61B 90/30* (2016.01)
*A61B 90/00* (2016.01)

(52) U.S. Cl.
CPC .......... *A61B 1/0615* (2013.01); *A61B 1/0638* (2013.01); *A61B 1/0676* (2013.01); *A61B 1/128* (2013.01); *A61B 5/06* (2013.01); *A61B 5/064* (2013.01); *A61B 90/30* (2016.02); *A61B 90/361* (2016.02); *A61B 2090/062* (2016.02)

(58) Field of Classification Search
USPC ......... 600/109, 160, 178–182; 362/554, 555, 362/572, 574
See application file for complete search history.

(56) References Cited

U.S. PATENT DOCUMENTS

| | | | |
|---|---|---|---|
| 5,554,220 A | 9/1996 | Forrest et al. | |
| 5,642,736 A | 7/1997 | Avitall | |
| 5,703,436 A | 12/1997 | Forrest et al. | |
| 5,707,745 A | 1/1998 | Forrest et al. | |
| 5,721,160 A | 2/1998 | Forrest et al. | |
| 5,757,026 A | 5/1998 | Forrest et al. | |
| 5,757,139 A | 5/1998 | Forrest et al. | |
| 5,811,833 A | 9/1998 | Thompson | |
| 5,834,893 A | 11/1998 | Bulovic et al. | |
| 5,844,363 A | 12/1998 | Gu et al. | |
| 5,861,219 A | 1/1999 | Thompson et al. | |
| 5,871,469 A | 2/1999 | Eggers et al. | |
| 5,874,803 A | 2/1999 | Garbuzov et al. | |
| 5,904,147 A | 5/1999 | Conlan et al. | |
| 5,917,280 A | 6/1999 | Burrows et al. | |
| 5,922,396 A | 7/1999 | Thompson | |
| 5,932,895 A | 8/1999 | Shen et al. | |
| 5,953,587 A | 9/1999 | Forrest et al. | |
| 5,981,306 A | 11/1999 | Burrows et al. | |
| 5,986,268 A | 11/1999 | Forrest et al. | |
| 5,986,401 A | 11/1999 | Thompson et al. | |
| 5,998,803 A | 12/1999 | Forrest et al. | |
| 6,005,252 A | 12/1999 | Forrest et al. | |
| 6,013,538 A | 1/2000 | Burrows et al. | |
| 6,013,982 A | 1/2000 | Thompson et al. | |
| 6,030,700 A | 2/2000 | Forrest et al. | |
| 6,030,715 A | 2/2000 | Thompson et al. | |
| 6,045,930 A | 4/2000 | Thompson et al. | |
| 6,046,543 A | 4/2000 | Bulovic et al. | |
| 6,048,630 A | 4/2000 | Burrows et al. | |
| 6,087,196 A | 7/2000 | Sturm et al. | |
| 6,091,195 A | 7/2000 | Forrest et al. | |
| 6,097,147 A | 8/2000 | Baldo et al. | |
| 6,111,902 A | 8/2000 | Kozlov et al. | |
| 6,124,046 A | 9/2000 | Jin et al. | |
| 6,125,226 A | 9/2000 | Forrest et al. | |
| 6,127,693 A | 10/2000 | Chen et al. | |
| 6,143,814 A | 11/2000 | Schiller et al. | |
| 6,150,043 A | 11/2000 | Thompson et al. | |
| 6,166,489 A | 12/2000 | Thompson et al. | |
| 6,185,443 B1 | 2/2001 | Crowley | |
| 6,210,814 B1 | 4/2001 | Thompson et al. | |
| 6,214,631 B1 | 4/2001 | Burrows et al. | |
| 6,232,714 B1 | 5/2001 | Shen et al. | |
| 6,242,115 B1 | 6/2001 | Thompson et al. | |
| 6,245,393 B1 | 6/2001 | Thompson et al. | |
| 6,259,202 B1 | 7/2001 | Sturm et al. | |
| 6,261,226 B1 | 7/2001 | McKenna et al. | |
| 6,264,805 B1 | 7/2001 | Forrest et al. | |
| 6,274,980 B1 | 8/2001 | Burrows et al. | |
| 6,287,712 B1 | 9/2001 | Bulovic et al. | |
| 6,294,398 B1 | 9/2001 | Kim et al. | |
| 6,297,516 B1 | 10/2001 | Forrest et al. | |
| 6,300,756 B2 | 10/2001 | Sturm et al. | |
| 6,303,238 B1 | 10/2001 | Thompson et al. | |
| 6,310,360 B1 | 10/2001 | Forrest et al. | |
| 6,312,836 B1 | 11/2001 | Bulovic et al. | |
| 6,329,085 B1 | 12/2001 | Burrows et al. | |
| 6,330,262 B1 | 12/2001 | Burrows et al. | |
| 6,331,156 B1 | 12/2001 | Haefele et al. | |
| 6,331,438 B1 | 12/2001 | Aylott et al. | |
| 6,333,521 B1 | 12/2001 | Thompson et al. | |
| 6,337,102 B1 | 1/2002 | Forrest et al. | |
| 6,350,875 B1 | 2/2002 | Weber et al. | |
| 6,358,631 B1 | 3/2002 | Forrest et al. | |
| 6,365,270 B2 | 4/2002 | Forrest et al. | |
| 6,366,268 B1 | 4/2002 | Forrest et al. | |
| 6,387,544 B1 | 5/2002 | Thompson et al. | |
| 6,396,860 B1 | 5/2002 | Kozlov et al. | |
| 6,403,392 B1 | 6/2002 | Burrows et al. | |
| 6,413,656 B1 | 7/2002 | Thompson et al. | |
| 6,420,031 B1 | 7/2002 | Parthasarathy et al. | |
| 6,449,006 B1 | 9/2002 | Shipp | |
| 6,495,198 B2 | 12/2002 | Peng | |
| 6,538,375 B1 * | 3/2003 | Duggal | C25D 7/0607 313/504 |
| 6,551,240 B2 | 4/2003 | Henzler | |
| 6,579,629 B1 | 6/2003 | Raychaudhuri et al. | |
| 6,613,002 B1 | 9/2003 | Clark et al. | |
| 6,620,497 B2 | 9/2003 | Smith et al. | |
| 6,627,333 B2 | 9/2003 | Hatwar | |
| 6,730,019 B2 | 5/2004 | Irion | |
| 6,814,699 B2 | 11/2004 | Ross et al. | |
| 6,951,536 B2 | 10/2005 | Yokoi et al. | |
| 6,964,501 B2 | 11/2005 | Ryan | |
| 7,553,276 B2 | 6/2009 | Iddan | |
| 2002/0038121 A1 | 3/2002 | Rozenburg et al. | |
| 2002/0120181 A1 | 8/2002 | Irion | |
| 2002/0133970 A1 | 9/2002 | Gordon et al. | |
| 2002/0143239 A1 | 10/2002 | Henzler | |
| 2002/0193664 A1 | 12/2002 | Ross et al. | |
| 2003/0036031 A1 | 2/2003 | Lieb et al. | |
| 2003/0095781 A1 | 5/2003 | Williams | |
| 2003/0125719 A1 | 7/2003 | Furnish | |
| 2003/0167000 A1 | 9/2003 | Mullick et al. | |
| 2004/0111132 A1 | 6/2004 | Shenderova et al. | |
| 2004/0196222 A1 | 10/2004 | Shih et al. | |
| 2004/0215059 A1 | 10/2004 | Homan et al. | |
| 2005/0043586 A1 | 2/2005 | Suzushima | |
| 2005/0106710 A1 | 5/2005 | Friedman et al. | |
| 2005/0137459 A1 | 6/2005 | Chin et al. | |
| 2005/0143623 A1 | 6/2005 | Kojima | |
| 2006/0069313 A1 | 3/2006 | Couvillon, Jr. et al. | |
| 2006/0098203 A1 | 5/2006 | Kalveram | |
| 2007/0185386 A1 | 8/2007 | Cheng | |

FOREIGN PATENT DOCUMENTS

| | | |
|---|---|---|
| GB | 2408209 A | 5/2005 |
| WO | WO 98/01412 | 1/1998 |
| WO | WO 98/34214 A1 | 8/1998 |
| WO | WO 03/019073 A1 | 3/2003 |
| WO | WO 03/075979 A2 | 9/2003 |
| WO | WO 2004/048881 | 6/2004 |
| WO | WO 2005/058149 A1 | 6/2005 |
| WO | WO 2007/092108 A2 | 8/2007 |

OTHER PUBLICATIONS

PCT International Search Report and Written Opinion for International Application No. PCT/US2007/000040, dated Jan. 10, 2007, 16 pages.

PCT International Search Report and Written Opinion for International Application No. PCT/US2004/041248, dated Mar. 24, 2005, 10 pages.

(56) References Cited

OTHER PUBLICATIONS

"SOLED Stacked Organic Light Emitting Device," Universal Display Corporation, Technology, Dec. 2001, (3 pages).

* cited by examiner

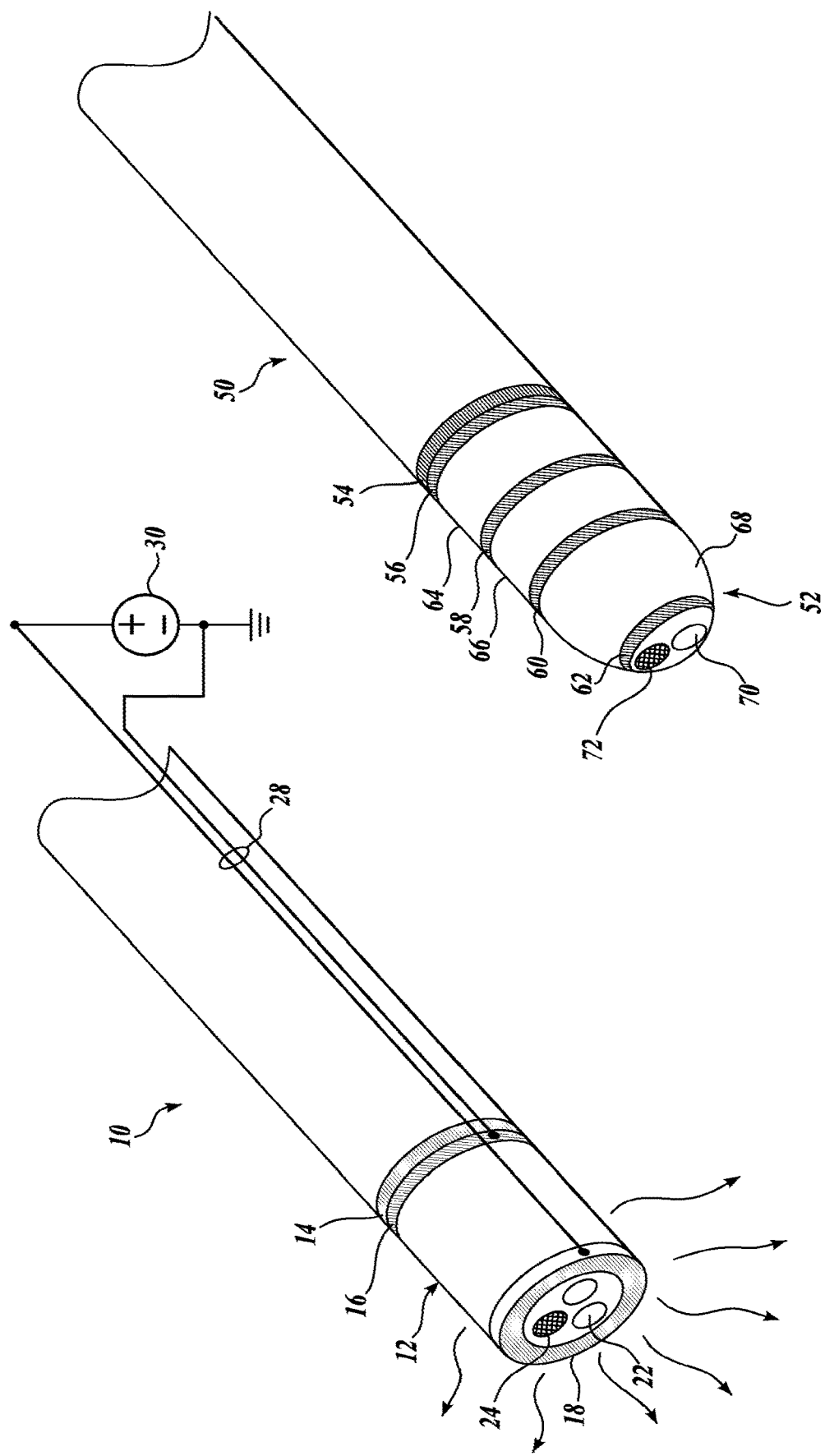

MEDICAL DEVICE WITH OLED ILLUMINATION LIGHT SOURCE

CROSS-REFERENCE TO RELATED APPLICATION

This application is a continuation of U.S. application Ser. No. 12/209,170, filed on Sep. 11, 2008, which is a divisional of U.S. patent application Ser. No. 10/737,980, filed Dec. 17, 2003, each of which is incorporated herein by reference in its entirety.

FIELD OF THE INVENTION

The present invention relates to medical devices in general, and illuminated catheters and endoscopes in particular.

BACKGROUND OF THE INVENTION

Many modern in-vivo medical devices such as catheters or endoscopes are equipped with imaging equipment that includes a light source and an image sensor. A light source delivers an illumination light onto an area of interest while the image sensor obtains an image from the reflected or scattered illumination light. The images obtained are used by a physician to diagnose internal body tissue or to perform surgical procedures in the body.

The most common type of light sources used on catheters and endoscopes are lasers or high powered white light sources. Light from these external light sources is delivered to the distal end of the scope by a fiber-optic illumination channel. Alternatively, some devices have solid state light sources such as light-emitting diodes (LEDs) that are located at or adjacent the distal tip of the device. Both approaches have limitations. First, the optical fibers used to form an illumination channel are relatively fragile and limit the bending ability of the device. On the other hand, LEDs are often encapsulated in a plastic or other transparent material that is relatively large in comparison to the size of the light-emitting element. Therefore, the amount of light that can be delivered at the distal end of the device is limited by the diameter of the device. Therefore, there is a need for a light-emitting device that can be incorporated into a medical device such as an endoscope that avoids these limitations.

SUMMARY OF THE INVENTION

To overcome the above-referenced limitations, the present invention is a flexible in-vivo medical imaging device such as a catheter or endoscope, having a light source made of one or more organic light-emitting diodes (OLEDs). An organic light-emitting diode is formed on the substrate between two or more semi-transparent electrodes. The organic light-emitting diode material produces illumination light when electrical energy is applied to the electrodes. The light source may comprise an OLED of a single color. Alternatively, the light source may be a stack or other configuration of OLEDs each having a different illumination wavelength such that one or more OLEDs can be energized at the same time to produce a desired illumination light. In another embodiment of the invention, the OLEDs are selected to produce excitation light in the ultraviolet wavelength band for fluorescence or drug-induced imaging. In yet another embodiment of the invention, the OLEDs produce light in the infrared range for tissue heating.

In one embodiment of the invention, the light source is sufficiently bright to allow external imaging devices to track the position of the light source as it is moved in the patient's body.

In another embodiment of the invention, the OLEDs are formed as strips that extend along the length of the device. The strips have distance markings thereon to gauge how far the device has been inserted into the patient.

In yet another embodiment of the invention, a catheter includes a heat conducting polymer to conduct heat away from the OLEDs and the patient.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 1 shows a medical device such as an endoscope having a single OLED light source at or adjacent its distal end in accordance with one embodiment of the present invention;

FIG. 2 illustrates a medical device having a light source comprising a number of OLEDs;

DETAILED DESCRIPTION OF THE PREFERRED EMBODIMENTS

Figure 3:
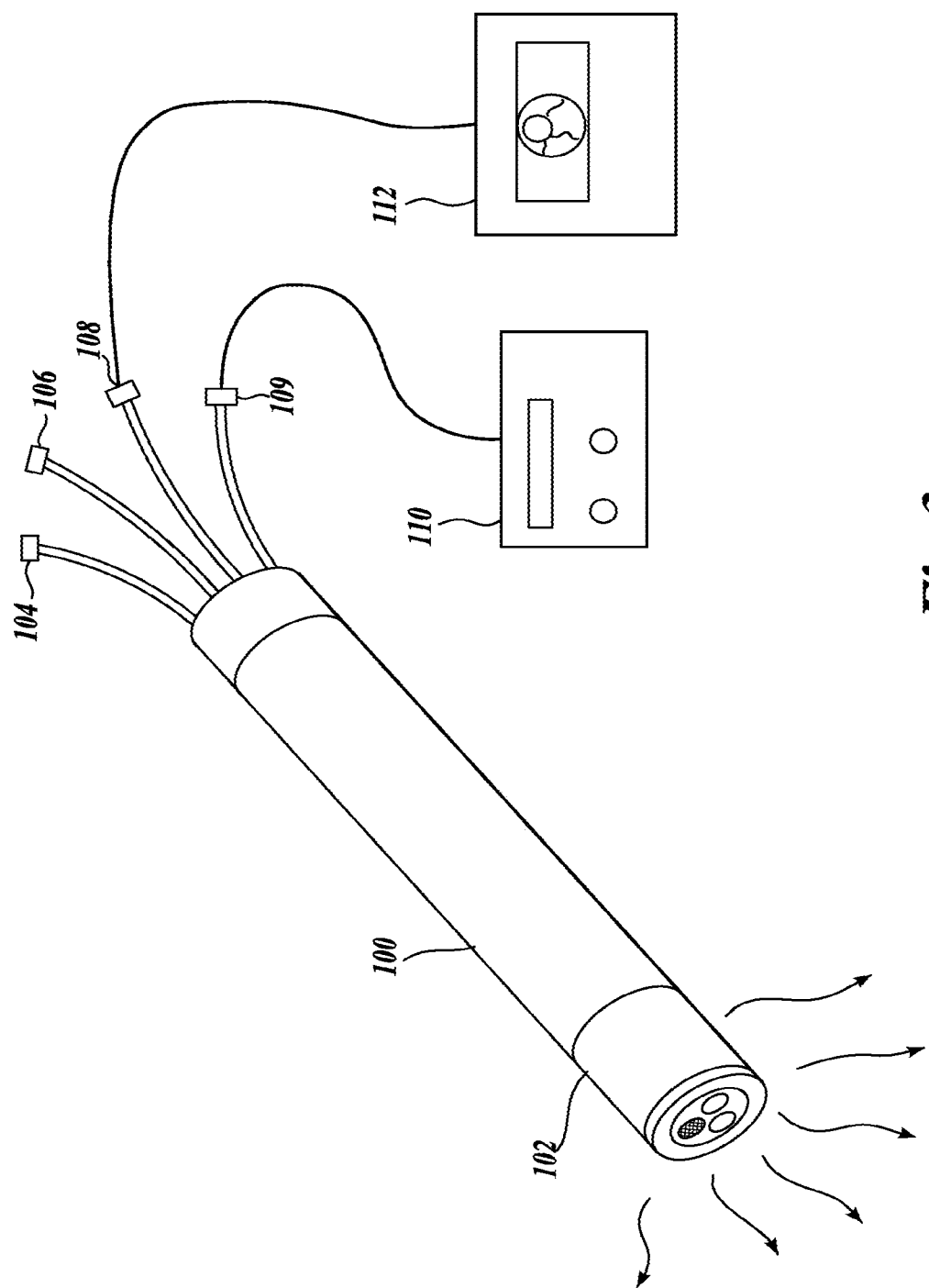
FIG. 3 shows components of an in-vivo medical imaging system, including an OLED light source in accordance with the present invention.

As indicated above, the present invention is an in-vivo medical device that uses organic light-emitting diodes (OLEDs) as a light source to provide illumination light within a patient's body cavity. FIG. 1 shows the distal end of an in-vivo medical device 10 such as a catheter, endoscope, bronchoscope, trocar, guidewire or other device that is inserted into a patient's body cavity. At or adjacent the distal end of the device is the light source 12 having one or more organic light-emitting diodes that produce illumination light when energized.

The light source 12 has a substrate 14 on which is formed an electrode 16. A semi-transparent electrode 18 is formed on top of the organic light-emitting diode material such that the diode material is sandwiched between the electrodes 16 and 18. Electrode wires, conductive leads, or other current carrying devices 28 connect the electrodes 16 and 18 to a power supply 30, which is typically external. However, the medical device could have built-in batteries to power the light source. The application of electrical energy to the electrodes 16 and 18 cause the organic light-emitting diode material to produce illumination light. The composition and method of constructing an OLED light source 12 suitable for use with the medical device of the present invention are known to those of ordinary skill in the art of light-emitting diodes. See, for example, U.S. Pat. Nos. 6,627,333; 6,124, 046; 6,127,693; and 6,495,198, which are herein incorporated by reference.

In the embodiment shown, the light source 12 is generally cylindrical or tubular in shape such that the medical device 10 can include one or more parallel or coaxial lumens 22 extending through the light source 12. In addition, the medical device 10 may include an image sensor 24 at or adjacent its distal end for capturing images of a patient. Alternatively, the medical device 10 may include an imaging light guide and one or more lenses that direct reflected and back scattered illumination light to an external image sensor or camera.

The illumination light provided by the light source 12 may be in the visible, ultraviolet or infrared spectrum depending upon the desired use of the medical device 10.

FIG. 2 illustrates another embodiment of a medical device 50 having an OLED light source 52 at or adjacent its distal end. The light source 52 includes a substrate 54 and a number of spaced, semi-transparent electrodes 56, 58, 60, 62. Between the electrodes are segments of organic light-emitting diode material of different colors or wavelengths in order to form a stacked organic light-emitting diode (SOLED). The color or illumination wavelength of the light induced by the light source 52 can be adjusted by applying a voltage to selected electrodes 56, 58, 60 or 62. The SOLED can be manufactured with known lithographic or semiconductor fabrication techniques such as those described in Patent Application No. PCT/US98/01412, which is herein incorporated by reference.

In the embodiment shown in FIG. 2, the light source 52 has an ovoidal shape with an atraumatic distal tip to reduce the likelihood of damaging tissue in the body. The medical device 50 also has one or more lumens 70 exiting the distal end of the device and an imaging sensor 72 for producing images of the patient.

FIG. 3 shows an in-vivo medical imaging system including a medical device 100 having a light source 102 formed of one or more OLEDs that provide illumination light to a point of interest in a patient's body. At the proximal end of the medical device 100 are the proximal openings of one or more lumens within the medical device 100, through which a physician can insert an instrument into the patient. In addition, the proximal end of the medical device includes a connector 109 that connects the light source 102 to a supply of electrical power 110. A connector 108 allows signals from an imaging sensor (not shown) at the distal end of the device to be connected to a video or other display 112.

In operation, the physician can adjust the supply of electrical power 110 to the one or more OLEDs at the distal end of the medical device 100 in order to adjust the intensity or illumination wavelength of the light produced. In some instances, the power supply 110 may be automatically controlled to illuminate the tissue with a number of different wavelengths such that images can be obtained with illumination light of each wavelength in order to view tissue under a variety of illumination conditions. Alternatively, the light source may be strobed to obtain images of moving tissue such as heart valves, etc.

Depending on the wavelength of the illumination light, different imaging techniques may be used to view or diagnose tissue in the body. These imaging techniques include: drug induced or native fluorescence imaging and white light or colored light imaging. In addition, light from the light source can be used to activate photosensitive drugs, or infrared heat can be supplied to tissue in the body.

Figure 4:
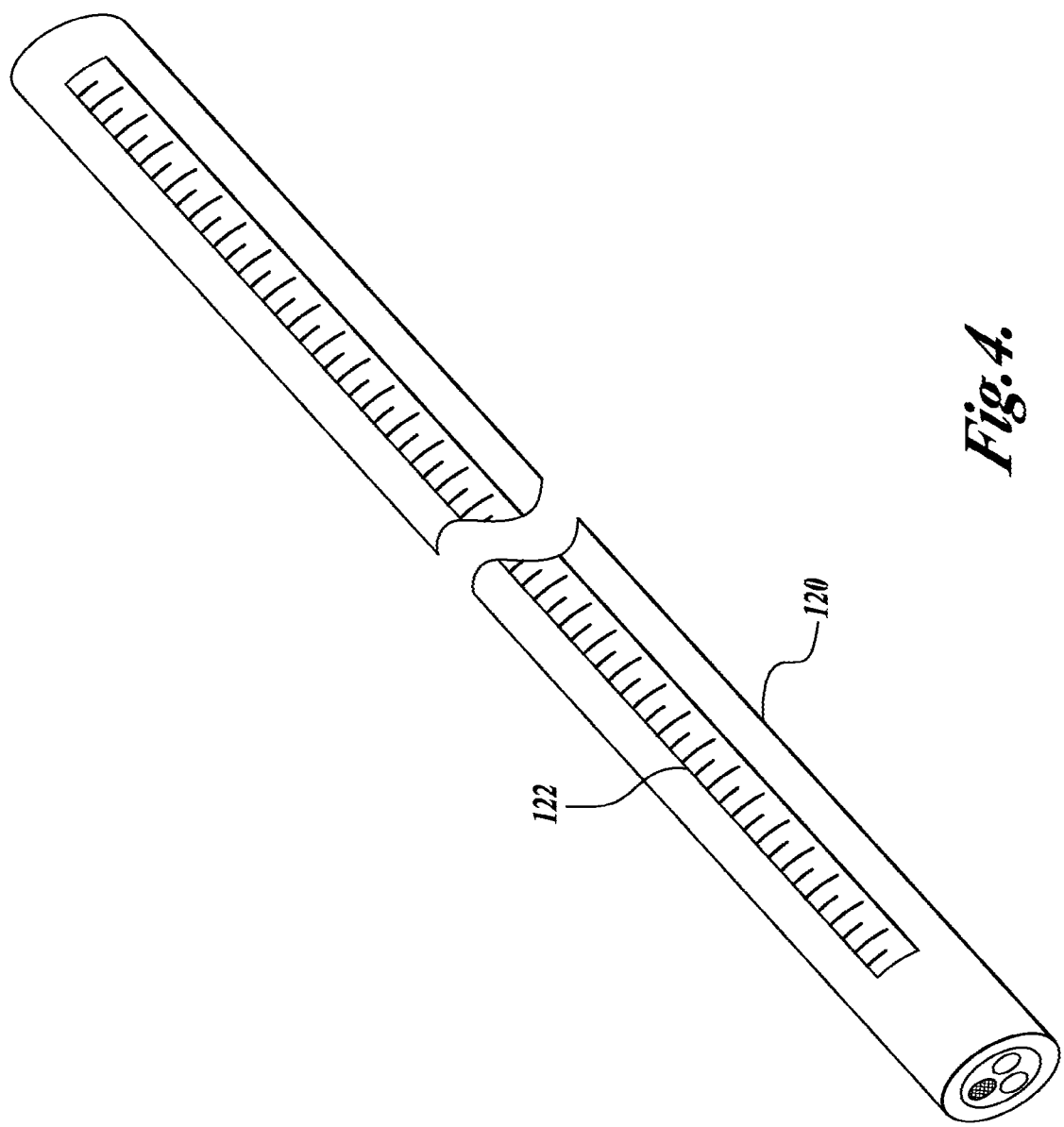
FIG. 4 shows a medical device including a strip of OLED material that can be used to gauge depth of insertion into a patient in accordance with another embodiment of the present invention.

FIG. 4 illustrates an embodiment of the invention whereby a medical device 120 has one or more strips of OLED material 122 positioned along its length. The strips 122 are preferably ruled or otherwise marked with distance indications. The one or more strips 122 can therefore be used to gauge how far the device 120 is inserted into a patient. The strip 122 may be integrally formed on the medical device 120 or may be separately formed by a semiconductor or lithographic process and secured to the device 120 with an adhesive or the like.

In the embodiments shown in FIGS. 1-4, it may be desirable to encapsulate the OLED light source with a transparent cover or shield to prevent bodily fluids from contacting the light source.

As will be appreciated, the OLEDs generate more light in a smaller area and with less heat than that produced by conventional LEDs. The light produced may be sufficient to externally view the position of the illuminated medical device inside the body with the naked eye or with external imaging equipment.

In some instances, it may be desirable to provide a mechanism for removing heat from the one or more OLEDs and transferring the heat to a point away from the patient's body. In one embodiment of the invention, the medical device includes a heat conducting polymer such as that described in U.S. Pat. No. 6,620,497 assigned to Cool Options, Inc. of Warwick, R.I., and which is herein incorporated by reference. A head conductive polymer as described in the '497 patent can be used to form the tubular walls of the medical device or a cover of the medical device. Alternatively, the medical device can include a strip of such a heat conductive polymer material having one end thermally coupled to the OLEDs and another end positioned away from the OLEDs. The strip therefore conducts the heat produced by the OLEDs away from the patient. The heat can be transferred outside of the patient's body or over a large enough area such that no point of the medical device that is within the patient becomes hot enough to cause discomfort or burn the patient.

Furthermore, the OLED endoscope may include a torqueable pull wire such as disclosed in U.S. Pat. No. 5,642,736, which is herein incorporated by reference, in order to provide the ability of an operator to bend the distal tip and to rotate it by torquing the wire or rotating it about its longitudinal axis.

While the preferred embodiment of the invention has been illustrated and described, it will be appreciated that various changes can be made therein without departing from the scope of the invention. For example, although the invention has been illustrated with endoscopes, it will be appreciated that other medical devices such as guide catheters, guidewires, ablation devices, balloon catheters or other devices could be equipped with such a light source. It is therefore intended that the scope of the invention be determined from the following claims and equivalents thereof.

The embodiments of the invention in which an exclusive property or privilege is claimed are defined at follows:

1. A medical illumination device comprising:
   a tubular member extending from a proximal end to a distal end;
   a substrate;
   a first electrode located on the substrate;
   a first lead coupled to the first electrode;
   a first LED, wherein the first LED radially surrounds a length of an outer surface of the tubular member and extends distally of the first electrode;
   a second electrode, wherein the first LED is directly connected to the first electrode and the second electrode; and
   a second lead coupled to the second electrode.

2. The medical illumination device of claim 1, further comprising a second LED.

3. The medical illumination device of claim 2, wherein the first LED and the second LED are spaced apart from one another along the length of the outer surface of the tubular member.

4. The medical illumination device of claim 1, wherein the first LED is an organic LED.

5. The medical illumination device of claim 1, wherein the first LED is one of a plurality of LEDs, and wherein each of the plurality of LEDs is configured to produce a first wavelength of light.

6. The medical illumination device of claim 1, further comprising a second LED, wherein the first LED is configured to produce a first light having a first wavelength, and the second LED is configured to produce a second light having a second wavelength, different than the first wavelength.

7. The medical illumination device of claim 1, further comprising a heat conductive polymer that is thermally coupled to the first LED.

8. The medical illumination device of claim 1, wherein the first LED is one of a plurality of LEDs, and wherein the tubular member defines a lumen extending through each of the plurality of LEDs.

9. The medical illumination device of claim 1, further including one or more lumens extending from the proximal end to the distal end of the tubular member.

10. The medical illumination device of claim 1, wherein the first LED is located longitudinally between the first electrode and the second electrode.

11. The medical illumination device of claim 1, wherein the second electrode is located on a distally-facing surface at the distal end of the tubular member.

12. The medical illumination device of claim 11, wherein the second electrode extends around a periphery of the distally-facing surface.

13. The medical illumination device of claim 11, further including a light source and an image sensor at the distally-facing surface.

14. The medical illumination device of claim 1, wherein the first electrode extends circumferentially around the substrate.

15. A medical illumination device comprising:
a tubular member having a proximal end and a distal end, wherein the distal end is dimensioned for insertion into a body cavity;
a first electrode located at a distal region of the tubular member, the first electrode configured to be coupled to a supply of electrical power; and
a first LED, wherein the first LED extends distally of the first electrode on the tubular member, and is configured to illuminate at different wavelengths in response to different levels of electrical power provided by the supply;
wherein the tubular member defines one or more lumens extending through the first LED.

16. The medical illumination device of claim 15, further comprising a heat conductive polymer that is thermally coupled to the first LED.

17. The medical illumination device of claim 15, wherein the first LED encircles a length of an outer surface of the tubular member.

18. The medical illumination device of claim 15, wherein the first LED is one of a plurality of LEDs, wherein each of the plurality of LEDs is organic.

* * * * *